US011085023B2

(12) United States Patent
Yamahara et al.

(10) Patent No.: US 11,085,023 B2
(45) Date of Patent: Aug. 10, 2021

(54) BOVINE SERUM COMPOSITION AND METHOD FOR CULTURING CELLS USING SAID BOVINE SERUM COMPOSITION AS ADDITIVE

(71) Applicant: Kenichi Yamahara, Kyoto (JP)

(72) Inventors: Kenichi Yamahara, Kyoto (JP); Shigeo Sudo, Fukuyama (JP); Toshita Sudo, Fukuyama (JP); Tomoharu Hiroshima, Fukuyama (JP)

(73) Assignee: Kenichi Yamahara, Kyoto (JP)

( * ) Notice: Subject to any disclaimer, the term of this patent is extended or adjusted under 35 U.S.C. 154(b) by 67 days.

(21) Appl. No.: 15/776,662

(22) PCT Filed: Nov. 16, 2016

(86) PCT No.: PCT/JP2016/083990
§ 371 (c)(1),
(2) Date: May 16, 2018

(87) PCT Pub. No.: WO2017/086356
PCT Pub. Date: May 26, 2017

(65) Prior Publication Data
US 2018/0371417 A1 Dec. 27, 2018

(30) Foreign Application Priority Data
Nov. 16, 2015 (JP) .............................. JP2015-224075

(51) Int. Cl.
A61K 35/16 (2015.01)
A61K 35/19 (2015.01)
A61K 35/17 (2015.01)
C12N 5/0775 (2010.01)

(52) U.S. Cl.
CPC ............ C12N 5/0662 (2013.01); A61K 35/16 (2013.01); A61K 35/17 (2013.01); A61K 35/19 (2013.01); C12N 2500/00 (2013.01); C12N 2501/115 (2013.01); C12N 2501/135 (2013.01); C12N 2501/15 (2013.01); C12N 2501/165 (2013.01); C12N 2501/20 (2013.01); C12N 2501/21 (2013.01); C12N 2501/22 (2013.01); C12N 2501/2301 (2013.01); C12N 2501/231 (2013.01); C12N 2501/2304 (2013.01); C12N 2501/2305 (2013.01); C12N 2501/2306 (2013.01); C12N 2501/2307 (2013.01); C12N 2501/2308 (2013.01); C12N 2501/2309 (2013.01); C12N 2501/2312 (2013.01); C12N 2501/2313 (2013.01); C12N 2501/24 (2013.01); C12N 2501/25 (2013.01)

(58) Field of Classification Search
CPC ......... A61K 35/16; A61K 35/17; A61K 35/19
See application file for complete search history.

(56) References Cited

U.S. PATENT DOCUMENTS

| 5,733,545 A | 3/1998 | Hood, III |
| 2002/0054916 A1 | 5/2002 | Peled et al. |
| 2005/0142208 A1 | 6/2005 | Yoo et al. |
| 2007/0048387 A1 | 3/2007 | Edwards et al. |
| 2010/0120150 A1 | 5/2010 | Suzuki et al. |
| 2010/0260815 A1 | 10/2010 | Kyle et al. |

FOREIGN PATENT DOCUMENTS

| JP | H11-502435 A | 3/1999 |
| JP | 2001-505906 A | 5/2001 |
| JP | 2005-530768 A | 10/2005 |
| JP | 2008-246200 A | 10/2008 |
| JP | 2009-506992 A | 2/2009 |
| JP | 2010-531142 A | 9/2010 |
| JP | 2011-160799 A | 8/2011 |
| JP | 2013-132240 A | 7/2013 |
| JP | 2013-132241 A | 7/2013 |
| JP | 2014-117347 A | 6/2014 |
| WO | WO 2014/126931 A1 | 8/2014 |

OTHER PUBLICATIONS

Roche, "An Investigation of Centrifugal Blood-Cell Separation" (May 2001), New Jersey Institute of Technology, 1-121 (Year: 2001).*

Eppley et al. "Platelet Quantification and Growth Factor Analysis from Platelet-Rich Plasma: Implication for Wound Healing" (Nov. 2004) Plastic and Reconstructive Surgery, vol. 114, No. 6:1502-1508. (Year: 2004).*

Margolis Initiation of Blood Coagulation by Glass and Related Surfaces, (1957) J. Physiology, vol. 137: 95-109. (Year: 1957).*

Loh et al., "Lysates Produced From Irradiated and Expired Buffy Coat-Derived Platelets Stored in Additive Solution Support Cell Proliferation," Vox Sanguinis, 109(Suppl. 1): 198, Abstract No. P-328 (2015).

Sousa et al., "Valorization of Outdated Blood Products for Regenerative Medicine," Vox Sanguinis, 101(Suppl. 1): 49, Abstract No. 4A-S14-05 (2011).

Japanese Patent Office, International Search Report in International Patent Application No. PCT/JP2016/083990 (dated Feb. 14, 2017).

(Continued)

Primary Examiner — Teresa E Knight
(74) Attorney, Agent, or Firm — Leydig, Voit & Mayer, Ltd.

(57) ABSTRACT

Provided is a method for producing an economical bovine serum composition containing many factors useful for cell proliferation. The method includes a step of performing an anticoagulation treatment of bovine whole blood with an anticoagulant, a step of obtaining a buffy coat and a fraction with a heavier specific gravity than that of the buffy coat from the anticoagulated whole blood, and a step of promoting and activating an interaction between the obtained leukocytes and platelets at a given temperature for not less than a given time to cause secretion or release of a humoral factor from the leukocytes and/or platelets and performing a recoagulation treatment of blood components including the humoral factor with a re-coagulating agent.

14 Claims, 3 Drawing Sheets

(56) References Cited

OTHER PUBLICATIONS

Japanese Patent Office, Notification of Reasons for Refusal in Japanese Patent Application No. 2017-507906 (dated Aug. 1, 2017).
CHEM17, "Operation instructions of kits for separating peripheral blood and organ tissue leukocytes of various animals" [obtained at http://www.chem17.com/st118460/Article_422439.html] (Oct. 24, 2012), Office Action in CN 201680066959.2 (dated Feb. 22, 2019).
Chinese Patent Office, First Office Action in Chinese Patent Application No. 201680066959.2 (dated Feb. 22, 2019).
Rocky Mountain Biologicals, "Comparison of FBS and Other Bovine Serums" (downloaded from https://www.rmbio.com/comparison-of-fbs-and-other-bovine-serums on Feb. 18, 2020).
Wappler et al., "Eliminating the need of serum testing using low serum culture conditions for human bone marrow-derived mesenchymal stromal cell expansion," *BioMedical Engineering OnLine*, 12: 15 (2013).
European Patent Office, Communication pursuant to Article 94(3) EPC in European Patent Application No. 16866357.3 (dated Sep. 19, 2019)).
Janetzko et al., "Fully automated processing of buffy-coat-derived pooled platelet concentrates," *Transfusion*, 44(7): 1052-1058 (2004).
Kocaoemer et al., "Human AB Serum and Thrombin-Activated Platelet-Rich Plasma Are Suitable Alternatives to Fetal Calf Serum for the Expansion of Mesenchymal Stem Cells from Adipose Tissue," *Stem Cells*, 25(5): 1270-1278 (2007).
European Patent Office, Extended European Search Report in European Patent Application No. 16866357.3 (dated Oct. 30, 2018).

\* cited by examiner

BOVINE SERUM COMPOSITION AND METHOD FOR CULTURING CELLS USING SAID BOVINE SERUM COMPOSITION AS ADDITIVE

CROSS-REFERENCE TO RELATED APPLICATIONS

This patent application is the U.S. national phase of International Patent Application No. PCT/JP2016/083990, filed Nov. 16, 2016, which claims the benefit of Japanese Patent Application No. 2015-224075, filed on Nov. 16, 2015, which are incorporated by reference in their entireties herein.

TECHNICAL FIELD

The present invention relates to a bovine serum composition and a method for culturing cells by using the bovine serum composition as an additive.

BACKGROUND ART

It is known that addition of bovine serum to the medium is effective for proliferation of cultured cells. In particular, fetal bovine serum contains many humoral factors including growth factors and has become the standard for cell culture.

However, due to the problem of bovine spongiform encephalopathy (BSE), fetal bovine serum produced in Oceania (countries other than those where BSE occurred) are widely used, thus leading to a soaring price. While adult bovine serum, which is not derived from fetus, can also be used for cell culture, it is known that adult bovine serum does not contain humoral factors including growth factors as much as fetal bovine serum does.

On the other hand, it has been reported that a medium added with platelet-rich plasma (PRP) prepared by concentrating platelets to high concentrations by centrifugation or the like of human whole blood after anticoagulation treatments is useful for culture and proliferation of cells (non-patent document 1).

Platelet-rich plasma contains large amounts of platelet-derived transforming growth factor-β (TGF-β), platelet-derived growth factor-BB (PDGF-BB), vascular endothelial cell growth factor (VEGF), epidermal growth factor (EGF) and the like, which induce cell proliferation (non-patent document 2).

Besides the above-mentioned growth factors, platelet contains a chemotactic factor called platelet factor 4 (PF4) for neutrophil and monocyte, and induces activation of leukocytes (non-patent document 3).

The components of blood cell contained in the whole blood also include leukocyte in addition to platelet. Leukocyte secretes platelet-activating factor (PAF) as well as interleukin, interferon and colony stimulating factor, and PAF is known to activate platelet (non-patent document 4).

A buffy coat is obtained from anticoagulated human whole blood with the process of standing, simple centrifugation treatment or the like. In the case of human, it is a white layer containing both platelet and leukocyte at high concentrations since its specific gravity is clearly different from that of plasma and erythrocyte. Thus, a serum in which platelets and leukocytes within the buffy coat layer are mutually activated, and which abundantly contains various humoral factors including growth factors, chemotactic factors, activation factors and the like secreted by the abovementioned platelets and leukocytes, is considered appropriate for cell culture.

In the case of bovine, however, the specific gravity of erythrocyte is lighter than that of human as mentioned below, and the specific gravity of leukocyte and that of erythrocyte partly overlap. As a result, the buffy coat contains fewer leukocytes and forms an indefinite layer. To recover both leukocytes and platelets, therefore, it is necessary to also harvest fractions having a heavier specific gravity than that of the buffy coat (=fractions containing leukocytes in the case of bovine), as clarified in the present invention.

In recent years, therapeutic application of cell formulations as products for regenerative medicine has been expected. On the other hand, it has been reported that intravenous administration, for example, of cells not normally present induces blood coagulation (non-patent document 5). Therefore, it is important for realization of regenerative medicine to establish a method of cell culture that is less likely to induce blood coagulation.

Patent document 1 describes a proliferation stimulant containing liquid components of coagulated umbilical cord blood. The stimulant promotes proliferation of mesenchymal stem cells. In patent document 1, an erythrocyte sedimentation agent is added to non-coagulated umbilical cord blood to separate the blood into a fraction containing erythrocytes and a supernatant fraction. The supernatant fraction is separated into a sediment fraction containing hematopoietic stem cells and a liquid fraction containing platelets. Then, the liquid fraction containing platelets is contacted with glass beads to produce the proliferation stimulant. That is, the proliferation stimulant does not contain the sediment fraction in which leukocytes with hematopoietic stem cells are present. On the other hand, the present invention provides a serum component obtained by, as mentioned below, activating interaction of leukocytes and platelets in a buffy coat at a given temperature for not less than a given time, and performing a recoagulation treatment of blood components including an obtained humoral component. Thus, the present invention is completely different from the invention described in patent document 1.

Patent document 2 describes a method of separating a serum by removing platelet-rich plasma and material components from the blood containing an anticoagulant, and feeding an adsorption member composed of a glass material into the resulting plasma to remove fibrinogen in the plasma by adsorption. In patent document 2, attachment of fibrinogen to the surface of a glass material is utilized and a glass material is used as an adsorption material to remove fibrinogen in the plasma. In the present invention, as mentioned below, the glass material is added to further activate the interaction of leukocytes and platelets in the buffy coat. Thus, the present invention is completely different from the invention to described in patent document 2.

In patent document 3, a concentrated serum is obtained by centrifuging collected human blood before coagulation without adding an anticoagulant, removing 80% of the plasma from the supernatant, suspending remaining blood components including platelets well, and adding glass beads as a blood coagulation promoting material to activate the platelets, coagulate the blood and release growth factors from the aforementioned platelets.

In addition, in patent document 4, an anticoagulant is added to the collected human blood, the blood is centrifuged, 80% of the plasma in the supernatant is removed, remaining blood components including platelets are suspended well, an aqueous calcium chloride solution is added as a blood coagulation promoting material to activate the platelets and coagulate the blood while releasing growth factors from the aforementioned platelets, whereby a concentrated serum is obtained. In the present invention, as mentioned below, in bovine blood added with an anticoagulant, a serum component is obtained by harvesting a fraction with comparatively wide range of a specific gravity including the buffy coat and a fraction with a heavier specific gravity than that of the buffy coat (including leukocytes in the case of bovine), activating interaction of leukocytes and platelets at a given temperature for not less than a given time, and performing a recoagulation treatment of blood components including an obtained humoral component. Thus, the present invention is completely different from the inventions described in patent documents 3 and 4.

DOCUMENT LIST

Patent Documents patent document 1: JP-A-2011-160799
patent document 2: JP-A-2006-104106
patent document 3: JP-A-2014-118362
patent document 4: JP-A-2014-117347

Non-Patent Documents non-patent document 1: Tissue Eng Part C Methods. 2009 September; 15(3):431-5.
non-patent document 2: Plast Reconstr Surg. 2004; 114: 1502-1508.
non-patent document 3: Proc Natl Acad Sci USA. 1981 July; 78(7):4584-7.
non-patent document 4: Nature. 1974 Jun. 7; 249(457):581-2.
non-patent document 5: Biochem Biophys Res Commun. 2013 Feb. 8; 431(2):203-9

SUMMARY OF THE INVENTION

Problems to be Solved by the Invention

The present invention provides an unconventional method for producing a bovine serum composition, and specifically aims to provide a production method of an economical bovine serum composition containing many factors useful for cell proliferation and many factors suppressing blood coagulation by cells.

Means of Solving the Problems

The production method of a bovine serum composition of the present invention characteristically includes a step of performing an anticoagulation treatment of bovine whole blood with an anticoagulant, a step of obtaining a buffy coat and a fraction with a heavier specific gravity than that of the buffy coat from the anticoagulated bovine whole blood, and a step of activating an interaction between the obtained leukocytes and platelets at a given temperature for not less than a given time to cause secretion or release of a humoral factor from the leukocytes and/or platelets and performing a recoagulation treatment of blood components including the humoral factor with a re-coagulating agent.

Effect of the Invention

A bovine serum composition obtained by the production method of a bovine serum composition of the present invention is economical and contains many cell growth factors. According to the present invention, for example, a serum composition having a proliferation promoting action equivalent to or more than that of fetal bovine serum can be produced from bovine whole blood. Fetal bovine serum is obtained by killing fetus(es). Thus, blood tests for infections in consideration of a window period (blank period during which infection cannot be confirmed by performing a test) cannot be performed afterwards. However, in the case of, for example, infection with a window period of 3 months in breeding cattles, the infection can be completely ruled out by performing a blood test 3 months after production of the serum composition, whereby a serum composition with high safety can be obtained. Therefore, a bovine serum composition obtained by the present invention is equivalent to or more than fetal bovine serum in the low costs, safety and cell growth potentiation. Also, it does not easily induce blood coagulation by the cells. The bovine serum composition obtained by the present invention is extremely superior as an additive for cell culture.

Figure 1:
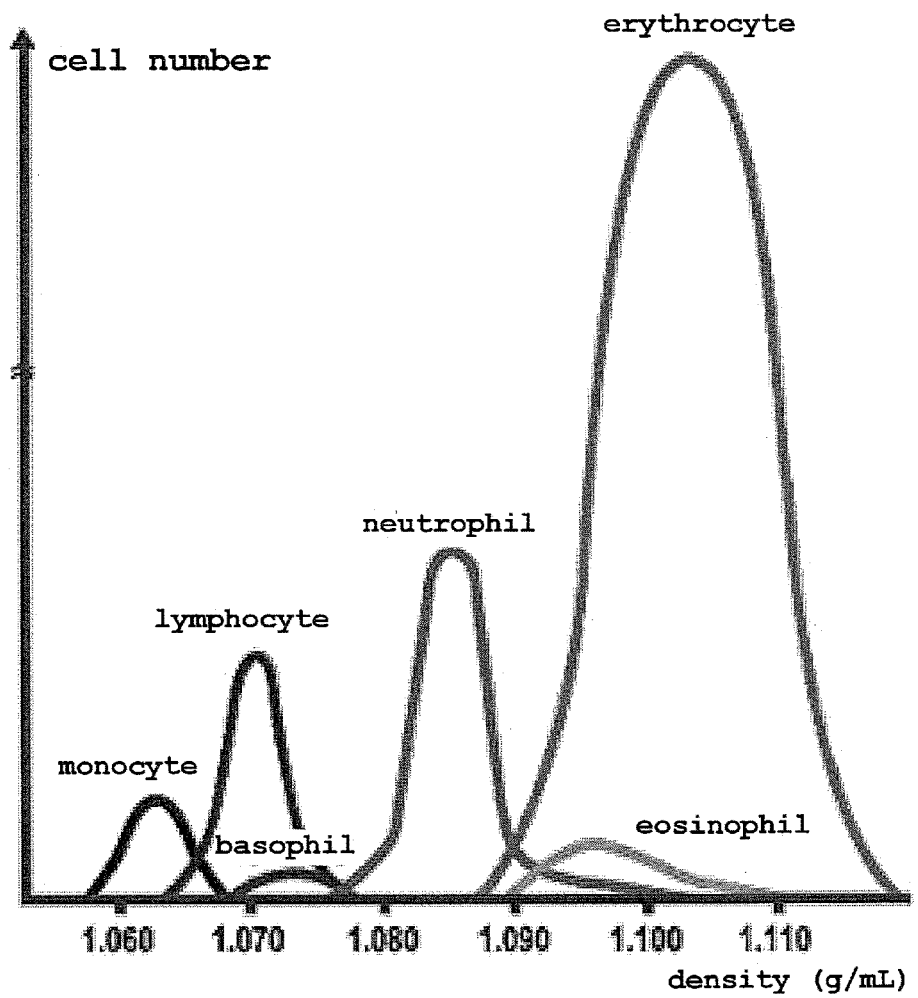
FIG. 1 shows the specific gravity of each blood component of human.

DESCRIPTION OF EMBODIMENTS (Production Method of Serum Composition)

The embodiments of the present invention are specifically explained below by referring to the attached Figures. The embodiments intend to facilitate understanding of the principle of the present invention. The scope of the present invention is not limited to the following embodiments, and other embodiments in which those of ordinary skill in the art appropriately substitute the constitution of the following embodiments are also encompassed in the scope of the present invention.

A bovine serum composition of this embodiment is obtained by
(i) anticoagulation treatment step: treating bovine whole blood with an anticoagulant,
(ii) leukocytes and platelets obtaining step: obtaining a buffy coat and a fraction with a heavier specific gravity than that of the buffy coat from the anticoagulated whole blood, and
(iii) leukocytes and platelets activation and recoagulation treatment step: activating interaction of the obtained leukocytes and platelets at a given temperature for not less than a given time, optionally with the addition or placement of a glass material, to cause secretion or release of a humoral factor from the leukocytes and/or platelets and performing a recoagulation treatment of blood components including the humoral factor with a re-coagulating agent. Each step is explained below.
(i) Anticoagulation Treatment Step
Whole blood is derived from bovine, and any of adult, juvenile, newborn and fetal bovines is applicable. By inserting a needle into the blood vessel, the whole blood can be collected from the needle through a tube into a blood collection bag and the like. The whole blood consists of components of blood cell (erythrocytes, leukocytes, platelets) and plasma as a liquid component. While the plasma contains a coagulation component, the serum hardly contains a coagulation component or a small amount of a liquid even when it does.

The anticoagulation treatment using an anticoagulant is performed during or after collecting the bovine whole blood. This aims at prevention of blood coagulation when the buffy coat is obtained from the whole blood as mentioned below since the blood contains blood coagulation factors such as fibrinogen (blood coagulation factor I), prothrombin (blood coagulation factor II), blood coagulation factor V, blood coagulation factor VIII and the like. The anticoagulant is not particularly limited and, for example, sodium citrate, citric acid, heparin and the like can be mentioned.

(ii) Leukocyte and Platelet Obtaining Step

Leukocytes and platelets are obtained from anticoagulated bovine whole blood by, for example, centrifuge or continuous centrifuge. A buffy coat is a layer of leukocytes and platelets formed between the erythrocyte layer and plasma when uncoagulated blood is centrifuged. In the case of bovine, however, the specific gravity of erythrocyte is lighter than that of human as mentioned below, and the specific gravity of leukocyte and that of erythrocyte partly overlap. As a result, the buffy coat contains fewer leukocytes and forms an indefinite layer. To recover both leukocytes and platelets, therefore, it is necessary to also harvest a fraction having a heavier specific gravity than that of the buffy coat (=a fraction containing leukocytes in the case of bovine), as clarified in the present invention. As mentioned below, the specific gravity of bovine platelets is, for example, 1.032-1.058, the specific gravity of bovine leukocyte is, for example, 1.032-1.084, and the specific gravity of bovine erythrocyte is, for example, 1.071-1.110. In the case of bovine whole blood, therefore, the buffy coat present between the erythrocyte layer and plasma has a specific gravity of 1.032-1.071. Since this layer contains fewer leukocytes, a fraction having a heavier specific gravity than that of the buffy coat, for example, 1.071-1.084, is also obtained. Thus, plasma containing large amounts of both leukocytes and platelets is prepared by removing plasma and erythrocytes having a heavy specific gravity from the anticoagulated bovine whole blood by, for example, centrifuge or continuous centrifuge.

In such adjustment in human, a clear difference exists in the specific gravity of each blood component (see the following Table 1 and FIG. 1), based on which each blood component is easily separated by standing for a long time or a simple centrifugal operation, and a buffy coat floating between erythrocyte and plasma and containing large amounts of leukocytes and platelets can be obtained easily.

TABLE 1

| | specific gravity |
|---|---|
| plasma | 1.025-1.029 |
| platelet | 1.032 |
| leukocyte | 1.063-1.085 |
| erythrocyte | 1.090-1.120 |

On the other hand, in the case of bovine, which shows small difference in the specific gravity among respective blood components, recovery of only leukocytes and platelets by an operation similar to that for human is difficult. For example, in the case of bovine, erythrocyte and leukocyte have specific gravity ranges overlapping in many portions as mentioned below, and they are difficult to separate. However, they can be obtained using a continuous centrifuge capable of continuously centrifuging more blood even when the difference in the specific gravity among blood components is only a little.

The conditions of centrifugation are not particularly limited and, for example, they can be at a centrifugal acceleration of 2900-11760 $m/s^2$ (300-1200×g), a temperature of 4-37° C., for a time of 3 min or longer.

(iii) Leukocyte and Platelet Activation, Recoagulation Treatment Step

Then, the obtained plasma containing large amounts of leukocytes and platelets is stood at ambient temperature to 40° C. for a given time to promote an interaction between the leukocytes and platelets. As used herein, the ambient temperature means 10° C.-30° C. In this case, the interaction between the leukocytes and platelets is further activated by contact with a glass material and the like, and a large amount of humoral factor is secreted or released from the leukocytes and/or platelets. The glass material is glass having a component made of soda-lime glass, lead glass, borosilicate glass, or mixture of these.

The contact of leukocytes and platelets with the glass material is a concept encompassing (i) adding a glass material to the buffy coat, (ii) adding a glass rod formed of a glass material to the buffy coat and stirring the buffy coat with the glass rod, (iii) adding the buffy coat into a glass material container formed of a glass material as the material.

While the temperature, time condition for the activation is desirably 37° C. for 1 hr or more, it can be, for example, ambient temperature to 40° C. for 5 min or more, or 37° C. to 40° C. for 1 to 3 hr, furthermore, 38° C. to 40° C. for 1 to 3 hr. It is also possible to simultaneously perform the next recoagulation treatment step by adding a re-coagulating agent during the activation time.

The shape of the glass material to be added is not particularly limited and, for example, it may be a shape of a granulated material, a sheet, a block or the like. The granulated material may be of, for example, a standard shape such as glass bead shape, marble shape, flattened marble shape, dice shape, cylindrical shape, prismatic shape, hollow cylindrical shape, doughnut shape, teardrop shape, plate shape and the like, or a non-standard shape such as cullet and the like. Preferred is a glass bead. The particle size of the granulated material is not particularly limited and may be, for example, 1-20 mm, preferably 5-9 mm.

The humoral factor secreted and released after concentration increase by adding a glass material include that derived from platelet, derived from leukocyte, or derived from both of these. The platelet-derived humoral factor includes, for example, TGF-beta1, Basic FGF, G-CSF, IFN-gamma, IL-10, IL-1RA, IL-1b, IL-4, IL-6, IL-8, TNF-alpha and the like. The leukocyte-derived humoral factor includes, for example, Eotaxin, IL-12 (p70) and the like. The humoral factor derived from both the platelet and leukocyte includes, for example, IL-5, IL-9, IP-10, MCP-1, PDGF-BB and the like.

Simultaneously, to obtain serum components as the supernatant, the aforementioned blood components including a humoral factor are applied to a recoagulation treatment with a re-coagulating agent. The re-coagulating agent is not particularly limited and can be appropriately determined according to the kind of the anticoagulant. For example, calcium chloride, protamine and the like can be mentioned. When the anticoagulant is citric acid, the re-coagulating agent is preferably, for example, calcium solution such as calcium chloride solution and the like. When the anticoagulant is heparin, the re-coagulating agent is preferably, for example, protamine and the like.

A bovine serum composition obtained through the aforementioned steps contains many cell growth factors and a serum composition with superior cell growth potentiation can be obtained. Furthermore, induction of blood coagulation by the obtained cells is suppressed and the safety is higher.

(Cell Culture Method)

The cell culture method of the present invention includes a step of promoting cell proliferation and suppressing induction of blood coagulation by culturing cells in a medium containing, as an additive, a bovine serum composition obtained by the production method of the bovine serum composition of the present invention.

The cell is not particularly limited and is, for example, a mesenchymal stem cell or a mesenchymal cell derived from bone marrow, adipose tissue or fetal appendage including amnion membrane and umbilical cord. The source of the cell is not particularly limited and, for example, human and rodents, domestic animals, non-human mammals such as primates excluding human and the like, and the like can be mentioned.

A medium containing the bovine serum composition as an additive is not particularly limited and is, for example, a medium usable for culturing mesenchymal stem cells. Specifically, for example, a-Minimal essential medium (aMEM medium), Dulbecco's modified eagle medium (DMEM medium) and the like can be mentioned.

The concentration of the bovine serum composition in a medium is not particularly limited. The concentration of the humoral factor contained in the serum composition may be, for example, 0.01-20 v/v %. The cell number per 1 mL medium may be, for example, 1000-100000.

The cell culture conditions are not particularly limited and, for example, the temperature is 37° C. and the time is 2-10 days. The medium is preferably exchanged with a new medium every, for example, 1-5 days. The method of medium exchange is, for example, a method for changing the medium every given time, a method for supplying a new medium continuously or intermittently or the like. In the latter case, for example, a part of the old medium is preferably discarded continuously or intermittently when the new medium is supplied.

EXAMPLES

Example 1

Using a blood component centrifuge (Component Collection system: CCS, manufactured by Haemonetics), various concentrations of leukocyte and platelet fractions were collected from anticoagulated blood, the leukocytes and platelets were mutually activated, serum compositions were prepared by a recoagulation treatment, and humoral factors therein were analyzed.

To be specific, an dedicated blood circuit (971J, manufactured by Haemonetics) for the centrifuge was mounted, an anticoagulant ACD-solution A (sodium citrate hydrate 2.20%, citric acid hydrate 0.80%, glucose 2.20%, manufactured by Terumo corporation) and the donor blood were mixed at a ratio of 1:10, the obtained anticoagulated blood was continuously centrifuged using a centrifugation bowl equipped to the blood circuit, and the resulting various concentrations of leukocyte and platelet fractions were collected separately over time. The obtained leukocyte and platelet fractions (buffy coat) were applied to an automatic blood cell counter (LC-660, manufactured by FUKUDA DENSHI) to measure the number of leukocytes and platelets. The results are shown in Table 2.

TABLE 2

| sample | leukocyte number (/µL) | ratio to sample A | platelet number (/µL) | ratio to sample A |
| --- | --- | --- | --- | --- |
| A | 14,000 | 100% | 2,910,000 | 100% |
| B | 21,000 | 150% | 3,280,000 | 113% |
| C | 24,000 | 171% | 2,830,000 | 97% |
| D | 17,000 | 121% | 1,490,000 | 51% |

As shown in Table 2, various concentrations of leukocyte and platelet fractions could be obtained from the anticoagulated blood by using the blood component centrifuge once.

To the obtained leukocyte and platelet fractions were added (with glass) or were not added (without glass) glass beads (one per blood component 50 ml: BZ-6, manufactured by AS ONE), 1 M aqueous calcium chloride solution was further added to a final addition concentration of 10 mM and the mixture was stood at ambient temperature for not less than 1 hr. After confirmation of coagulation, the mixture was centrifuged at 3000 rpm for 10 min, and the supernatant (serum composition) was recovered and preserved at −80° C. The serum composition was thawed, and the TGF-beta1 concentration was measured by TGF-beta1 ELISA kit (#88-8350-22, manufactured by Affimetrix). The results are shown in Table 3.

TABLE 3

| | TGF-beta1 concentration (ng/ml) | | | |
| --- | --- | --- | --- | --- |
| sample | without glass | ratio to sample A | with glass | ratio to sample A |
| A | 178.5 | 100% | 196.0 | 100% |
| B | 185.7 | 104% | 200.1 | 102% |
| C | 168.2 | 94% | 185.7 | 95% |
| D | 87.1 | 49% | 108.5 | 55% |

As shown in Table 3, the TGF-beta1 concentration was sufficient even without glass but showed an increase in the concentration when glass was used. Referring to the ratio to sample A, a high correlation was found with the data of the platelet number in Table 2, thus suggesting that many TGF-beta1s in the serum composition were derived from platelet. By comparison of samples A and C, the platelet count and the concentration of TGF-beta1 were almost the same number, and it was strongly suggested that TGF-beta1 was derived from platelet.

Furthermore, the serum compositions were subjected to an comprehensive cytokine analysis (Basic FGF, Eotacin, G-CSF, GM-CSF, IFN-gamma, IL-10, IL-12 (p70), IL-13, IL-15, IL-17, IL-1RA, IL-1b, IL-2, IL-4, IL-5, IL-6, IL-7, IL-8, IL-9, IP-10, MCP-1, MIP-1a, MIP-1b, PDGF-BB, RANTES, TNF-alpha, VEGF) using Bio-Plex Pro human cytokine 27-Plex assay (#M50-0KCAF0Y, manufactured by Bio-Rad) (excluding GM-CSF, IL-15, IL-17, IL-2, MIP-1a since almost all samples were below detection sensitivity). The results are shown in Tables 4-25.

TABLE 4

Basic FGF concentration (pg/ml)

| sample | without glass | ratio to sample A | with glass | ratio to sample A |
|---|---|---|---|---|
| A | 8.3 | 100% | 53.5 | 100% |
| B | — | — | 70.0 | 131% |
| C | — | — | 60.5 | 113% |
| D | 16.7 | 200% | 35.3 | 66% |

As shown in Table 4, the Basic FGF concentration showed a significant increase when glass was used. Referring to the ratio to sample A, with glass, a high correlation was found with the data of the platelet number in Table 2, thus suggesting that Basic FGFs in the serum composition were mainly derived from platelet. By comparison of samples A and C (with glass), the platelet count and the concentration of Basic FGF were almost the same number, and it was strongly suggested that TGF-beta1 was derived from platelet.

TABLE 5

Eotaxin concentration (pg/ml)

| sample | without glass | ratio to sample A | with glass | ratio to sample A |
|---|---|---|---|---|
| A | 83.2 | 100% | 90.4 | 100% |
| B | 90.6 | 109% | 134.9 | 149% |
| C | 125.7 | 151% | 128.5 | 142% |
| D | 124.4 | 150% | 109.6 | 121% |

As shown in Table 5, the Eotaxin concentration was sufficient even without glass but showed an increase in the concentration when glass was used. Referring to the ratio to sample A, a high correlation was found with the data of the leukocyte in Table 2, thus suggesting that Eotaxins in the serum composition were mainly derived from leukocyte. By comparison of samples B and C (with glass), the leukocyte count and Eotaxin concentration were almost the same number, and it was strongly suggested that Eotaxin was derived from leukocyte.

TABLE 6

G-CSF concentration (pg/ml)

| sample | without glass | ratio to sample A | with glass | ratio to sample A |
|---|---|---|---|---|
| A | 43.7 | 100% | 115.2 | 100% |
| B | 18.8 | 43% | 166.1 | 144% |
| C | 37.9 | 87% | 135.3 | 117% |
| D | 62.4 | 143% | 82.6 | 72% |

As shown in Table 6, the G-CSF concentration showed a significant increase when glass was used. Referring to the ratio to sample A, with glass, a high correlation was found with the data of the platelet number in Table 2, thus suggesting that G-CSFs in the serum composition were mainly derived from platelet. By comparison of samples A and C, the platelet count and the concentration of G-CSF were almost the same number, and it was strongly suggested that G-CSF was derived from platelet.

TABLE 7

IFN-gamma concentration (pg/ml)

| sample | without glass | ratio to sample A | with glass | ratio to sample A |
|---|---|---|---|---|
| A | 100.9 | 100% | 237.7 | 100% |
| B | 51.6 | 51% | 336.3 | 141% |
| C | 87.7 | 87% | 275.7 | 116% |
| D | 103.5 | 103% | 188.2 | 79% |

As shown in Table 7, the IFN-gamma concentration showed a significant increase when glass was used. Referring to the ratio to sample A, with glass, a high correlation was found with the data of the platelet number in Table 2, thus suggesting that IFN-gammas in the serum composition were mainly derived from platelet. By comparison of samples A and C, the platelet count and the concentration of IFN-gamma were almost the same number, and it was strongly suggested that IFN-gamma was derived from platelet.

TABLE 8

IL-10 concentration (pg/ml)

| sample | without glass | ratio to sample A | with glass | ratio to sample A |
|---|---|---|---|---|
| A | 9.6 | 100% | 25.3 | 100% |
| B | 11.2 | 117% | 36.0 | 142% |
| C | 14.0 | 146% | 29.9 | 118% |
| D | 12.2 | 127% | 18.9 | 75% |

As shown in Table 8, the IL-10 concentration showed a significant increase when glass was used. Referring to the ratio to sample A, with glass, a high correlation was found with the data of the platelet number in Table 2, thus suggesting that IL-10s in the serum composition were mainly derived from platelet. By comparison of samples A and C, the platelet count and the concentration of IL-10 were almost the same number, and it was strongly suggested that IL-10 was derived from platelet.

TABLE 9

IL-12 (p70) concentration (pg/ml)

| sample | without glass | ratio to sample A | with glass | ratio to sample A |
|---|---|---|---|---|
| A | 51.1 | 100% | 84.6 | 100% |
| B | 53.1 | 104% | 128.6 | 152% |
| C | 63.5 | 124% | 109.7 | 130% |
| D | 50.4 | 99% | 84.8 | 100% |

As shown in Table 9, the IL-12 (p70) concentration was sufficient even without glass but showed an increase in the concentration when glass was used. Referring to the ratio to sample A, a high correlation was found with the data of the leukocyte number in Table 2, thus suggesting that IL-12s (p70s) in the serum composition were mainly derived from leukocyte. By comparison of samples A and D, the leukocyte count and the concentration of IL-12 (p70) were almost the same number, and it was strongly suggested that IL-12 (p70) was derived from leukocyte.

TABLE 10

| | IL-13 concentration (pg/ml) | | | |
|---|---|---|---|---|
| sample | without glass | ratio to sample A | with glass | ratio to sample A |
| A | 8.5 | 100% | 12.9 | 100% |
| B | 6.5 | 76% | 17.1 | 133% |
| C | 9.0 | 106% | 14.2 | 110% |
| D | 8.3 | 98% | 11.1 | 86% |

As shown in Table 10, the IL-13 concentration showed a significant increase when glass was used. Referring to the ratio to sample A when glass was used, a high correlation was found in the data of the platelet number in Table 2, thus suggesting that IL-13s in the serum composition were mainly derived from platelet. By comparison of samples A and C, the platelet count and the concentration of IL-13 were almost the same number, and it was strongly suggested that IL-13 was derived from platelet.

TABLE 11

| | IL-1RA concentration (pg/ml) | | | |
|---|---|---|---|---|
| sample | without glass | ratio to sample A | with glass | ratio to sample A |
| A | 106.5 | 100% | 273.6 | 100% |
| B | 45.9 | 43% | 409.5 | 150% |
| C | 80.4 | 75% | 334.3 | 122% |
| D | 98.7 | 93% | 203.8 | 74% |

As shown in Table 11, the IL-1RA concentration showed a significant increase when glass was used. Referring to the ratio to sample A (with glass), a high correlation was found with the data of the platelet number in Table 2, thus suggesting that IL-1RAs in the serum composition were mainly derived from platelet. By comparison of samples A and C, the platelet count and the concentration of IL-1RA were almost the same number, and it was strongly suggested that IL-1RA was derived from platelet.

TABLE 12

| | IL-1b concentration (pg/ml) | | | |
|---|---|---|---|---|
| sample | without glass | ratio to sample A | with glass | ratio to sample A |
| A | 1.51 | 100% | 5.32 | 100% |
| B | 0.68 | 45% | 7.43 | 140% |
| C | 1.11 | 74% | 6.06 | 114% |
| D | 1.51 | 100% | 3.36 | 63% |

As shown in Table 12, the IL-1b concentration showed a significant increase when glass was used. Referring to the ratio to sample A, with glass, a high correlation was found with the data of the platelet number in Table 2, thus suggesting that IL-1bs in the serum composition were mainly derived from platelet. By comparison of samples A and C, the platelet count and the concentration of IL-1b were almost the same number, and it was strongly suggested that IL-1b was derived from platelet.

TABLE 13

| | IL-4 concentration (pg/ml) | | | |
|---|---|---|---|---|
| sample | without glass | ratio to sample A | with glass | ratio to sample A |
| A | 3.29 | 100% | 7.15 | 100% |
| B | 1.71 | 52% | 10.09 | 141% |
| C | 3.05 | 93% | 8.20 | 115% |
| D | 3.28 | 100% | 5.48 | 77% |

As shown in Table 13, the IL-4 concentration showed a significant increase when glass was used. Referring to the ratio to sample A (with glass), a high correlation was found with the data of the platelet number in Table 2, thus suggesting that IL-4s in the serum composition were mainly derived from platelet. By comparison of samples A and C, the platelet count and the concentration of IL-4 were almost the same number, and it was strongly suggested that IL-4 was derived from platelet.

TABLE 14

| | IL-5 concentration (pg/ml) | | | |
|---|---|---|---|---|
| sample | without glass | ratio to sample A | with glass | ratio to sample A |
| A | 7.4 | 100% | 12.3 | 100% |
| B | 3.1 | 42% | 17.0 | 138% |
| C | 5.5 | 74% | 15.2 | 124% |
| D | 5.6 | 76% | 10.3 | 84% |

As shown in Table 14, the IL-5 concentration showed a significant increase when glass was used. Referring to the ratio to sample A, a poor correlation to the data of the leukocyte number and platelet number in Table 2 is found irrespective of whether the glass was used. As the tendency, it is in a close relation to the platelet number. However, (1) when without glass, sample B shows higher platelet number but lower IL-5 concentration than other samples; (2) when with glass, a comparison of samples A and C reveals almost the same platelet number and the highest IL-5 concentration in sample C. From these, IL-5 is highly possibly derived from both leukocyte and platelet. As the basis for the derivation from the interaction due to glass use, the facts that, in sample C, high leukocyte number and platelet number equal to that of samples A and B is seen, but that IL-5 concentration is (1) smaller than others when without glass and (2) comparatively higher than others when with glass can be pointed out.

TABLE 15

| | IL-6 concentration (pg/ml) | | | |
|---|---|---|---|---|
| sample | without glass | ratio to sample A | with glass | ratio to sample A |
| A | 8.4 | 100% | 18.5 | 100% |
| B | 3.8 | 45% | 25.6 | 138% |
| C | 6.7 | 80% | 21.5 | 116% |
| D | 7.4 | 88% | 13.6 | 74% |

As shown in Table 15, the IL-6 concentration showed a significant increase when glass was used. Referring to the ratio to sample A (with glass), a high correlation was found with the data of the platelet number in Table 2, thus suggesting that IL-6s in the serum composition were mainly derived from platelet. By comparison of samples A and C, the platelet count and the concentration of IL-6 were almost the same number, and it was strongly suggested that IL-6 was derived from platelet.

TABLE 16

| | IL-7 concentration (pg/ml) | | | |
|---|---|---|---|---|
| sample | without glass | ratio to sample A | with glass | ratio to sample A |
| A | 21.5 | 100% | 23.1 | 100% |
| B | 20.4 | 95% | 26.4 | 114% |
| C | 24.6 | 114% | 23.3 | 101% |
| D | 15.2 | 71% | 18.3 | 79% |

As shown in Table 16, the IL-7 concentration was sufficient even without glass but showed no increase in the concentration when glass was used. However, referring to the ratio to sample A, a correlation was found with the data of the platelet number in Table 2, thus suggesting that IL-7s in the serum composition were mainly derived from platelet. By comparison of samples A and C, the platelet count and the concentration of IL-7 were almost the same number, and it was suggested that IL-7 was derived from platelet.

TABLE 17

| | IL-8 concentration (pg/ml) | | | |
|---|---|---|---|---|
| sample | without glass | ratio to sample A | with glass | ratio to sample A |
| A | 28.7 | 100% | 65.0 | 100% |
| B | 18.5 | 43% | 91.0 | 150% |
| C | 28.5 | 75% | 71.8 | 122% |
| D | 31.6 | 93% | 46.7 | 74% |

As shown in Table 17, the IL-8 concentration showed a significant increase when glass was used. Referring to the ratio to sample A (with glass), a high correlation was found with the data of the platelet number in Table 2, thus suggesting that IL-8s in the serum composition were mainly derived from platelet. By comparison of samples A and C, the platelet count and the concentration of IL-8 were almost the same number, and it was strongly suggested that IL-8 was derived from platelet.

TABLE 18

| | IL-9 concentration (pg/ml) | | | |
|---|---|---|---|---|
| sample | without glass | ratio to sample A | with glass | ratio to sample A |
| A | 9.2 | 100% | 22.4 | 100% |
| B | 9.3 | 101% | 32.6 | 146% |
| C | 14.8 | 161% | 27.1 | 121% |
| D | 14.7 | 160% | 18.8 | 84% |

As shown in Table 18, the IL-9 concentration was sufficient even without glass but showed an increase in the concentration when glass was used. Referring to the ratio to sample A, a poor correlation to the data of the leukocyte number and platelet number in Table 2 is found irrespective of whether the glass was used. As the tendency, (1) when without glass, it is in a close relation to the leukocyte number, but sample B shows higher platelet number than A and IL-9 concentration equal to that of A; (2) when with glass, it is in a close relation to the platelet number but a comparison of samples A and B reveals almost the same platelet number and the highest IL-9 concentration in sample B. From these, IL-9 is highly possibly derived from both leukocyte and platelet. As the basis for the derivation from the interaction due to glass use, the facts that, in sample B, relatively high leukocyte number and the highest platelet number is seen, but that IL-9 concentration is (1) small when without glass and (2) the highest when with glass can be pointed out.

TABLE 19

| | IP-10 concentration (pg/ml) | | | |
|---|---|---|---|---|
| sample | without glass | ratio to sample A | with glass | ratio to sample A |
| A | 855.7 | 100% | 1053.9 | 100% |
| B | 774.9 | 91% | 1605.6 | 152% |
| C | 967.0 | 113% | 1393.2 | 132% |
| D | 674.3 | 79% | 1228.3 | 117% |

As shown in Table 19, the IP-10 concentration was sufficient even without glass but showed an increase in the concentration when glass was used. Referring to the ratio to sample A, a correlation to the data of the leukocyte number and platelet number in Table 2 is hardly found. As the tendency, (1) when without glass, it is in a close relation to the leukocyte number, but sample D showed a half platelet number and about 80% IP-10 concentration compared to A; (2) when with glass, it is in a close relation to the leukocyte number, but a comparison of samples B and C reveals equal platelet number and difference in the IP-10 concentration. From these, IP-10 is highly possibly derived from both leukocyte and platelet. As the basis for the derivation from the interaction due to glass use, the facts that, in sample B, relatively high leukocyte number and the highest platelet number is seen, but that IP-10 concentration is (1) not more than average when without glass and (2) the highest when with glass can be pointed out.

TABLE 20

| | MCP-1 concentration (pg/ml) | | | |
|---|---|---|---|---|
| sample | without glass | ratio to sample A | with glass | ratio to sample A |
| A | 30.0 | 100% | 59.4 | 100% |
| B | 27.5 | 92% | 83.8 | 141% |
| C | 44.7 | 149% | 74.0 | 125% |
| D | 48.2 | 161% | 56.2 | 95% |

As shown in Table 20, the MCP-1 concentration was sufficient even without glass but showed an increase in the concentration when glass was used. Referring to the ratio to sample A, a poor correlation to the data of the leukocyte number and platelet number in Table 2 is found irrespective of whether the glass was used. (1) when without glass, the MCP-1 concentration of sample D is the highest and shows no correlation with the leukocyte number and platelet number; (2) when with glass, as the tendency, it is in a close relation to the platelet number, but a comparison of samples A and C reveals the same platelet number but 25% difference in the MCP-1 concentration. From these, MCP-1 is highly possibly derived from both leukocyte and platelet. AS the basis for the derivation from the interaction due to glass use, the facts that, in sample B, relatively high leukocyte number and the highest platelet number is seen, but that MCP-1 concentration is (1) the lowest when without glass and (2) the highest when with glass can be pointed out.

TABLE 21

| | MIP-1b concentration (pg/ml) | | | |
| --- | --- | --- | --- | --- |
| sample | without glass | ratio to sample A | with glass | ratio to sample A |
| A | 67.5 | 100% | 56.9 | 100% |
| B | 83.2 | 123% | 95.2 | 167% |
| C | 72.5 | 107% | 81.4 | 143% |
| D | 48.2 | 71% | 64.3 | 113% |

As shown in Table 21, the MIP-1b concentration showed no increase in the concentration when glass was used. However, referring to the ratio to sample A, a correlation was found with the data of the leukocyte number in Table 2, thus suggesting that MIP-1bs in the serum composition were mainly derived from leukocyte. By comparison of samples A and D, the leukocyte count and the concentration of MIP-1b were almost the same number, and it was suggested that MIP-1b was derived from leukocyte.

TABLE 22

| | PDGF-BB concentration (ng/ml) | | | |
| --- | --- | --- | --- | --- |
| sample | without glass | ratio to sample A | with glass | ratio to sample A |
| A | 10.8 | 100% | 11.7 | 100% |
| B | 7.9 | 73% | 12.1 | 103% |
| C | 12.9 | 119% | 11.4 | 97% |
| D | 8.9 | 82% | 11.2 | 96% |

As shown in Table 22, the PDGF-BB concentration was sufficient even without glass but showed an increase in the concentration when glass was used. Referring to the ratio to sample A, a poor correlation to the data of the leukocyte number and platelet number in Table 2 is found irrespective of whether the glass was used. (1) when without glass, the PDGF-BB concentration of sample B is the lowest and shows no correlation with the leukocyte number and platelet number; (2) when with glass, as the tendency, it is in a close relation to the leukocyte number, but a comparison of samples A and D reveals a half platelet number but equal PDGF-BB concentration. From these, PDGF-BB is highly possibly derived from both leukocyte and platelet. As the basis for the derivation from the interaction due to glass use, in sample B, relatively high leukocyte number and the highest platelet number is seen, but that PDGF-BB concentration is (1) the lowest when without glass and (2) the highest when with glass can be pointed out.

TABLE 23

| | RANTES concentration (ng/ml) | | | |
| --- | --- | --- | --- | --- |
| sample | without glass | ratio to sample A | with glass | ratio to sample A |
| A | 2.52 | 100% | 1.56 | 100% |
| B | 2.67 | 106% | 2.58 | 165% |
| C | 4.13 | 164% | 2.49 | 160% |
| D | 4.48 | 178% | 2.56 | 164% |

As shown in Table 23, the RANTES concentration showed no increase in the concentration when glass was used. Referring to the ratio to sample A, a correlation to the data of the leukocyte number and platelet number in Table 2 is not found. From these, the possibility that RANTES is derived from both leukocyte and platelet cannot be ruled out.

TABLE 24

| | TNF-alpha concentration (pg/ml) | | | |
| --- | --- | --- | --- | --- |
| sample | without glass | ratio to sample A | with glass | ratio to sample A |
| A | 24.3 | 100% | 47.6 | 100% |
| B | 13.8 | 57% | 63.4 | 133% |
| C | 19.7 | 81% | 52.6 | 111% |
| D | 19.4 | 80% | 36.3 | 76% |

As shown in Table 24, the TNF-alpha concentration showed a significant increase when glass was used. Referring to the ratio to sample A (with glass), a high correlation was found with the data of the platelet number in Table 2, thus suggesting that TNF-alphas in the serum composition were mainly derived from platelet. By comparison of samples A and C, the platelet count and the concentration of IL-8 were almost the same number, and it was strongly suggested that TNF-alpha was derived from platelet.

TABLE 25

| | VEGF concentration (pg/ml) | | | |
| --- | --- | --- | --- | --- |
| sample | without glass | ratio to sample A | with glass | ratio to sample A |
| A | 144 | 100% | 141 | 100% |
| B | 235 | 163% | 239 | 170% |
| C | 250 | 174% | 189 | 134% |
| D | 102 | 71% | 164 | 116% |

As shown in Table 25, the VEGF concentration showed no increase in the concentration when glass was used. Referring to the ratio to sample A, a correlation to the data of the leukocyte number and platelet number in Table 2 is hardly found. When without glass, the tendency is in a close relation to the leukocyte number. When, for example, samples A and D are compared, a correlation is not found between the platelet number and the VEGF concentration. Therefrom the possibility that VEGF is derived from both leukocyte and platelet cannot be ruled out.

These results are summarized in Table 26.

TABLE 26

| | | concentration increase by glass |
| --- | --- | --- |
| derived from leukocyte | Eotaxin, IL-12(p70), MIP-1b | other than MIP-1b |
| platelet-derived | TGF-beta1, Basic FGF, G-CSF, IFN-gamma, IL-10, IL-12, IL-1RA, IL-1b, IL-4, IL-6, IL-7, IL-8, TNF-alpha, | other than IL-7 |
| derived from both leukocyte and platelet | IL-5, IL-9, IP-10, MCP-1, PDGF-BB, RANTES, VEGF | other than RANTES, VEGF |

As in Table 26, addition of glass beads enhanced mutual interaction between leukocytes and platelets in components of blood cell containing the leukocytes and platelets, and it was clarified that many humoral factors are secreted and released.

Example 2

Furthermore, optimization of the temperature and time conditions in the mutual activation of the obtained leukocyte and platelet fractions was studied.

To be specific, in the same manner as in Example 1, a dedicated blood circuit (971J, manufactured by Haemonetics) for the centrifuge was mounted, an anticoagulant ACD-solution A (sodium citrate hydrate 2.20%, citric acid hydrate 0.80%, glucose 2.20%, manufactured by Terumo corporation) and the donor blood were mixed at a ratio of 1:10, and leukocyte and platelet fractions were collected by continuous centrifugation of the obtained anticoagulated blood by using a centrifugation bowl equipped to the blood circuit. To the obtained leukocyte and platelet fractions was added aqueous calcium chloride solution to a final addition concentration of 5 mM, and the mixture was stood (1) under each condition of 4° C., 20° C., 37° C., 40° C., 50° C. for 5 min, (2) under condition of 37° C. for 5 min, 1 hr, 6 hr. After confirmation of coagulation, the mixture was centrifuged at 3000 rpm for 10 min, and the supernatant (serum composition) was recovered and preserved at −80° C. The serum composition was thawed, and the TGF-beta1 concentration was measured by TGF-beta1 ELISA kit (#88-8350-22, manufactured by Affimetrix). The results are shown in Table.

TABLE 27

| temperature | time | TGF-beta1 concentration (ng/ml) |
|---|---|---|
| 4° C. | 5 min | 10.5 |
| 20° C. | 5 min | 60.7 |
| 37° C. | 5 min | 67.2 |
| 40° C. | 5 min | 69.8 |
| 50° C. | 5 min | 46.5 |
| 20° C. | 1 hr | 86.9 |
| 37° C. | 1 hr | 92.1 |
| 40° C. | 1 hr | 83.4 |
| 37° C. | 6 hr | 90.2 |

As shown in Table 27, the TGF-beta1 concentration was high at a temperature of 20° C. to 40° C. and the time of not less than 1 hr. From the above, the temperature and time conditions for the mutual activation of the leukocyte and platelet fractions are considered to be ambient temperature to 40° C. for not less than 1 hr.

Example 3

Difference due to animal species in the collection of leukocyte and platelet fractions from the anticoagulated whole blood was studied.

To be specific, anticoagulated blood (14 ml) obtained by mixing an anticoagulant ACD-solution A (sodium citrate hydrate 2.20%, citric acid hydrate 0.80%, glucose 2.20%, manufactured by Terumo corporation) and human or bovine blood at a ratio of 1:10 was added to a 15 ml polypropylene tube (2325-015, manufactured by AGC TECHNO GRASS Co. Ltd.), centrifuged (universal cooling centrifuge 5922, manufactured by KUBOTA Corporation) at 200×g, ambient temperature for 20 min, and the state was photographed. The results are shown in FIG. 2.

Figure 2:
FIG. 2 shows the results of centrifugation of the anticoagulated whole blood of bovine and human.

In FIG. 2, the left shows bovine and the right shows human. In normal centrifugation, bovine is judged to have a relatively low specific gravity of erythrocyte and erythrocytes do not form sediment easily. Human has a high erythrocyte specific gravity and erythrocytes easily form sediments. That is, in bovine, erythrocytes do not form sediment easily by standing or simple centrifugation operation, as a result of which it is assumed that comparatively lighter leukocyte and platelet fractions do not emerge easily.

Example 4

Figure 3:
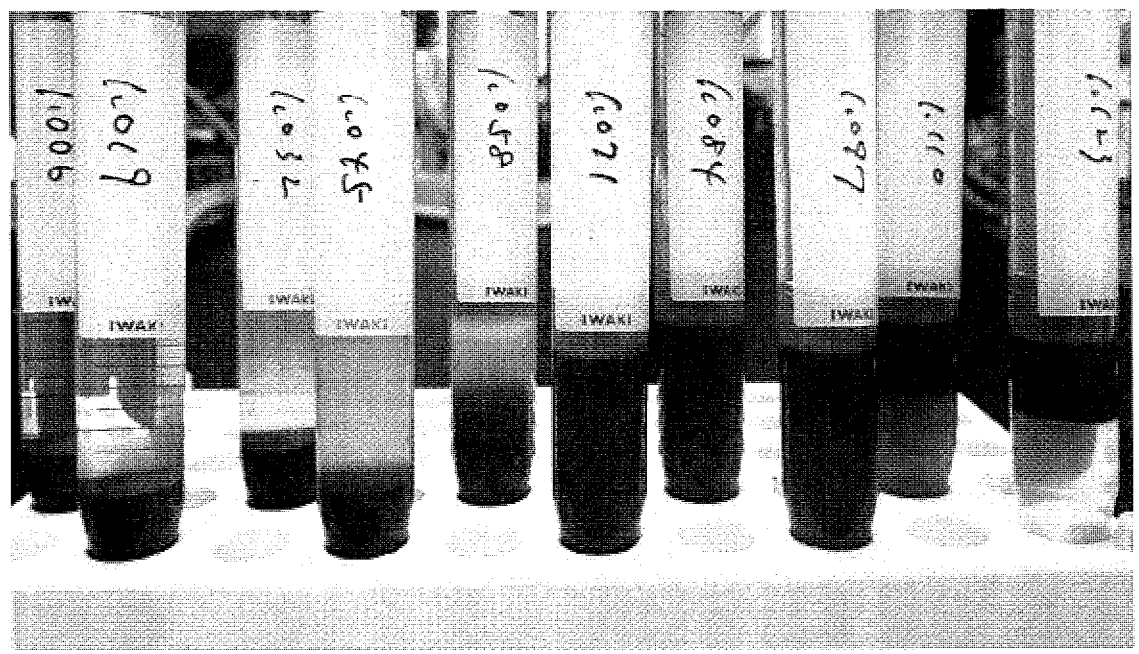
FIG. 3 shows the results of centrifugation of the anticoagulated whole blood of bovine at each specific gravity.

Accordingly, the specific gravity of each blood component in bovine was studied. Appropriate doses of Percoll stock solution (1.130 g/ml, manufactured by GE Healthcare Bioscience, 17-0891-01), 1.5 M NaCl, and sterilized water were mixed to prepare isotonic Percoll solutions having a specific gravity of 1.123, 1.110, 1.097, 1.084, 1.071, 1.058, 1.045, 1.032, 1019, 1.006. These isotonic Percoll solutions were added by 3 ml each into a 15 ml polypropylene tube (2325-015, manufactured by AGC TECHNO GRASS Co. Ltd.). Anticoagulated blood (3 ml) obtained by mixing an anticoagulant ACD-solution A (sodium citrate hydrate 2.20%, citric acid hydrate 0.80%, glucose 2.20%, manufactured by Terumo corporation) and bovine blood at a ratio of 1:10 was overlaid by 3 ml on a 15 ml polypropylene tube (2325-015, manufactured by AGC TECHNO GRASS Co. Ltd.) added with isotonic Percoll solution, centrifuged (universal cooling centrifuge 5922, manufactured by KUBOTA Corporation) at 400×g, ambient temperature for 10 min, and the state was photographed. The results are shown in FIG. 3.

As mentioned above, it was found that bovine blood contains many erythrocytes lighter than specific gravity 1.071 that float in an isotonic Percoll solution with specific gravity 1.071.

Furthermore, each tube (6 ml) was divided into the upper part (3 ml) and the bottom part (3 ml), and the components of blood cell in each of them were measured by an automatic blood cell counter (ProCyte Dx manufactured by IDEXX Laboratories). The results are shown in Table 28.

TABLE 28

| | Upper part | | | Bottom part | | |
|---|---|---|---|---|---|---|
| specific gravity | RBC (×10$^6$/μl) | WBC (×10$^3$/μl) | PLT (×10$^3$/μl) | RBC (×10$^6$/μl) | WBC (×10$^3$/μl) | PLT (×10$^3$/μl) |
| 1.123 | 7.14 | 9.03 | 117 | 0.08 | 0.1 | 0 |
| 1.11 | 6.73 | 8.7 | 129 | 0.32 | 0.15 | 0 |
| 1.097 | 6.16 | 8.67 | 116 | 1.36 | 0.49 | 1 |
| 1.084 | 4.95 | 8.01 | 124 | 2.45 | 1 | 3 |
| 1.071 | 3.23 | 7.25 | 124 | 4.17 | 1.75 | 3 |
| 1.058 | 0.04 | 1.76 | 108 | 7.72 | 7.71 | 32 |
| 1.045 | 0.01 | 1.42 | 78 | 7.64 | 7.85 | 59 |
| 1.032 | 0.01 | 0.19 | 71 | 7.72 | 9.2 | 65 |
| 1019 | 0 | 0 | 13 | 7.94 | 9.34 | 97 |
| 1.0058 | 0 | 0.01 | 2 | 7.6 | 9.02 | 87 |

From the results of Table 28, the specific gravity of each blood cell component of bovine is as shown in Table 29.

TABLE 29

| | specific gravity |
|---|---|
| bovine platelet | 1.032-1.058 |
| bovine leukocyte | 1.032-1.084 |
| bovine erythrocyte | 1.071-1.110 |

In this way, it was clarified that the investigation based on the results of FIG. 2 are correct, namely, in bovine, since erythrocytes have a comparatively light specific gravity. Thus, erythrocytes do not form sediment easily by standing or simple centrifugation operation.

Furthermore, it was clarified that, in human, leukocyte and platelet fractions (so-called buffy coat) emerge by a simple operation, whereas in bovine, since leukocyte and erythrocyte have specific gravity ranges overlapping in many portions, it is difficult to separate all leukocytes by standing or simple centrifugation operation.

Example 5

Thus, aiming at stable collection of leukocyte and platelet fractions from bovine whole blood, use of a continuous centrifuge was studied.

To be specific, a dedicated blood circuit (971J, manufactured by Haemonetics) was mounted on a blood component centrifuge (CCS, manufactured by Haemonetics), an anticoagulant ACD-solution A (sodium citrate hydrate 2.20%, citric acid hydrate 0.80%, glucose 2.20%, manufactured by Terumo corporation) and bovine whole blood were mixed at a ratio of 1:10, the obtained anticoagulated blood was continuously centrifuged using a centrifugation bowl equipped to the blood circuit, and emerged leukocyte and platelet fractions were photographed. The results are shown in FIG. 4.

Figure 4:
FIG. 4 shows the results of continuous centrifugation of the anticoagulated whole blood of bovine.

As shown in FIG. 4, a buffy coat (leukocyte and platelet fractions) drawing a white band-like circle is clearly present between erythrocytes on the outer side of the centrifugation bowl and the plasma on the inner side thereof. When a continuous centrifuge is used, a large amount of blood is treated at one time (>250 ml). Thus, it is assumed that the buffy coat appeared comparatively easily even when there was a slight difference in the specific gravity.

The fractions before and after the emerged buffy coat were separately collected over time (samples 1-8, each about 5 ml), and the components of blood cell in each of them were measured by an automatic blood cell counter (ProCyte Dx manufactured by IDEXX Laboratories). The results are shown in Table 30.

TABLE 30

| sample | RBC (×10$^6$/μl) | WBC (×10$^3$/μl) | PLT (×10$^3$/μl) | |
|---|---|---|---|---|
| before treatment | 8.92 | 14.6 | 136 | |
| 1 | 0.03 | 0.02 | 22 | ← platelets (small amount) |
| 2 | 0.03 | 0.01 | 35 | ← platelets (small amount) |
| 3 | 0.03 | 0.01 | 49 | ← platelets (small amount) |
| 4 | 0.03 | 0 | 50 | ← platelets (small amount) |
| 5 | 0.07 | 7.74 | 241 | ← leukocytes + platelets |
| 6 | 0.73 | 96.8 | 1107 | ← leukocytes + platelets (buffy coat) |
| 7 | 5.05 | 120 | 690 | ← erythrocytes + leukocytes + platelets |
| 8 | 8.81 | 61.3 | 260 | ← erythrocytes + leukocytes + platelets |

It was verified that sample 6 located in the buffy coat was a leukocyte+platelet fraction. It was also clarified that sample 6 with a specific gravity heavier than that of the buffy coat contained the largest number of leukocytes. As a result, it was confirmed that fractions having a heavier specific gravity (=containing leukocytes in the case of bovine) than that of the buffy coat need to be also collected to obtain many leukocytes and platelets from anticoagulated bovine whole blood.

Example 6

Thus, leukocyte and platelet fractions were collected from anticoagulated bovine whole blood by using a blood component centrifuge (CCS, manufactured by Haemonetics), activated by adding glass beads, a serum composition (hereinafter the present serum composition) was prepared by a recoagulation treatment, and the possibility as an additive aiming at cell culture was studied.

To be specific, a dedicated blood circuit (970E, manufactured by Haemonetics) for the centrifuge was mounted, anticoagulant Citramin solution "Fuso" 4% (sodium citrate hydrate 4%, manufactured by Fuso Pharmaceutical Industries, Ltd.) and bovine blood were mixed at a ratio of 1:16, and leukocyte and platelet fractions were collected by continuous centrifugation of the obtained anticoagulated blood by using a centrifugation bowl equipped to the blood circuit. To the obtained leukocyte and platelet fractions were added glass beads (one per blood component 50 ml: BZ-6, manufactured by AS ONE), aqueous calcium chloride solution was further added to a final addition concentration of 5 mM, and the mixture was stood at 37° C. for not less than 6 hr. After confirmation of coagulation, the mixture was centrifuged at 3000 rpm for 10 min, and the supernatant (serum composition) was recovered and preserved at −20° C. The serum composition was thawed, added to aMEM medium (manufactured by Life Technologies, 41061) at a proportion of 10% to give a medium for cell culture. As the control, aMEM medium added with fetal bovine serum (manufactured by Moregate Biotech) by 10% of the medium was used.

Figure 5:
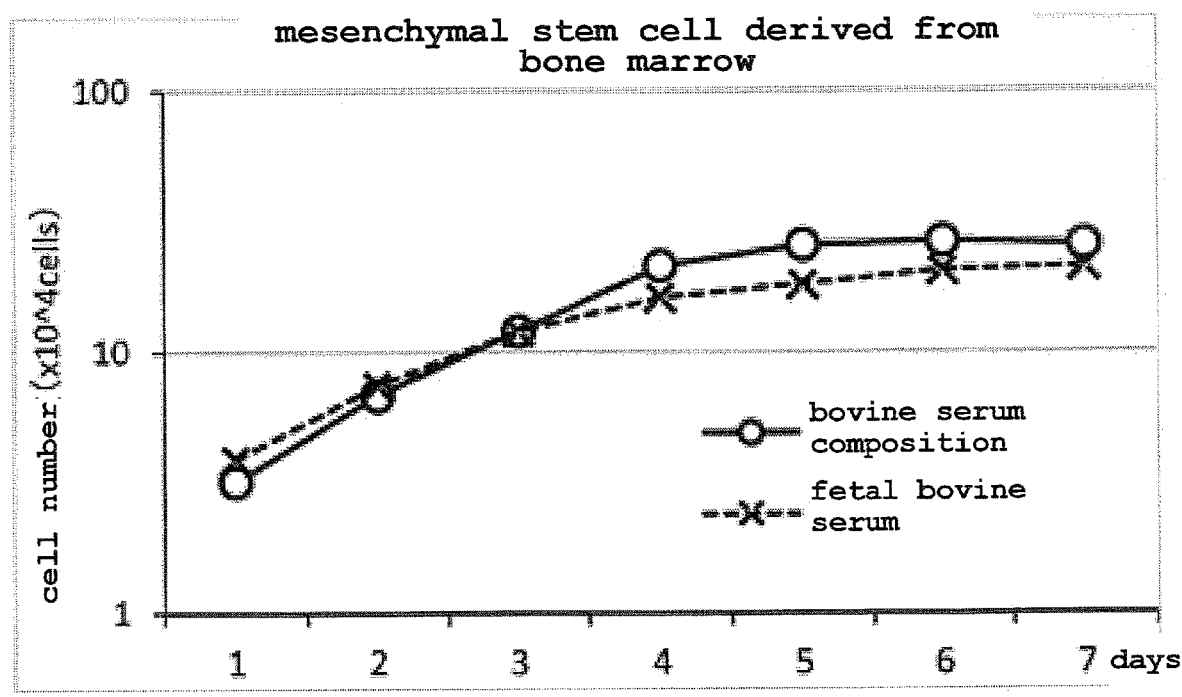
FIG. 5 shows a cell proliferation curve of mesenchymal stem cells derived from human bone marrow.
Figure 6:
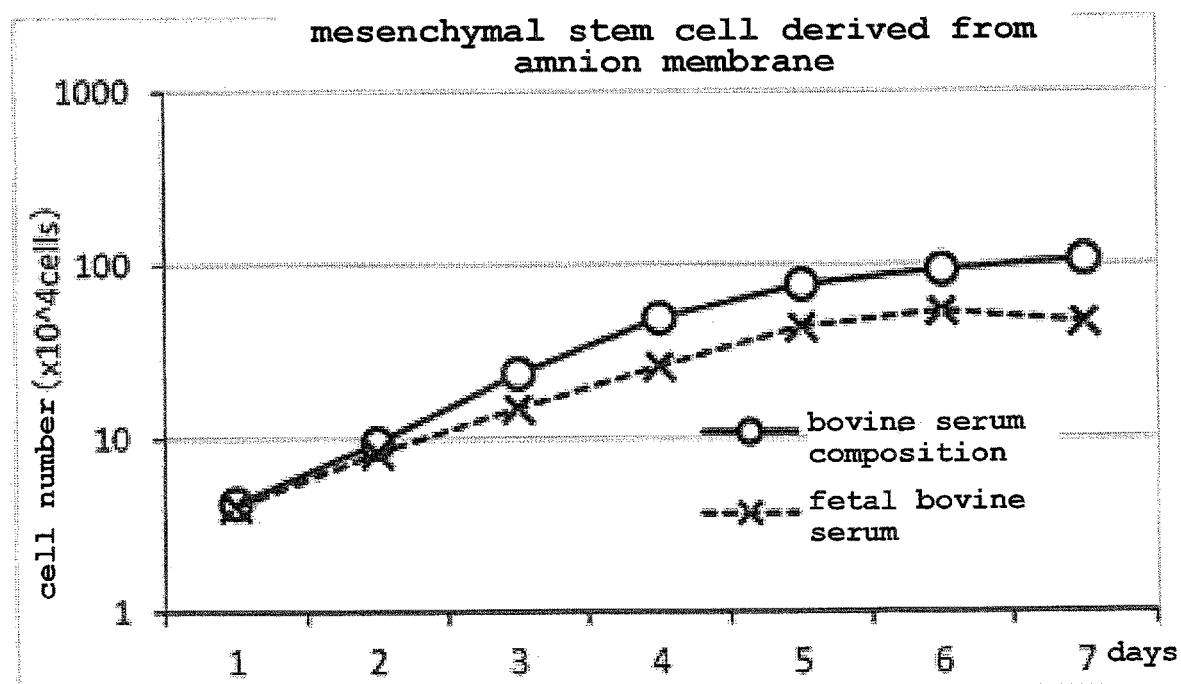
FIG. 6 shows a cell proliferation curve of mesenchymal stem cells derived from human amnion membrane.

For evaluation of a medium for cell culture, commercially available mesenchymal stem cells derived from human bone marrow (manufactured by Lonza, PT-2501) and the mesenchymal stem cells derived from human amnion membrane, which were established by us, were used to draw proliferation curves. The mesenchymal stem cells derived from human amnion membrane were cultured as in the following step. That is, amnion membrane obtained by cesarean operation was subjected to an enzyme treatment with collagenase and thermolysin at 35° C. for 30 min, cells were collected by passing the enzyme-treated amnion membrane through a mesh with pore size 100 μm, and the collected cells were cultured. The concentration of collagenase was 500 CDU/ml and the concentration of thermolysin was 400 PU/ml. The results are respectively shown in FIG. 5 and FIG. 6. As in FIG. 5 and FIG. 6, in any of the cultures of mesenchymal stem cells derived from bone marrow and amnion membrane, the present serum composition was found to be a serum composition superior in the cell growth potentiation as compared to the fetal bovine serum generally used for cell culture.

Example 7

In addition, the effect of the present serum composition on the cell diameter was studied. In the same manner as in the above-mentioned Example 6, mesenchymal stem cells derived from human amnion membrane, which were established by us, were cultured using aMEM medium added with the present serum composition (aMEM medium added with 10% fetal bovine serum as the control) by 10% of the medium and passaged as appropriate. An average cell diameter (μm) was measured for each passage and difference between the two was examined. The results are shown in Table 31.

TABLE 31

| passage number | 3 | 4 | 5 | 6 | 7 |
|---|---|---|---|---|---|
| fetal bovine serum | 24.3 | 17.6 | 18.7 | 19.2 | 25.1 |
| present serum composition | 18.7 | 17.1 | 15.3 | 18.1 | 15.9 |

The mesenchymal stem cells derived from human amnion membrane and cultured in the present serum composition showed a constantly small cell diameter for each passage as compared to fetal bovine serum. In Example 6, the present serum composition was shown to have strong cell growth potentiation as compared to fetal bovine serum, for which the short time before cell division was considered to be the reason.

Example 8

In intravenous administration of a cell preparation using cultured mesenchymal stem cells, promotion of blood coagulation by the administrated cells often poses a problem. Thus, whether the cell cultured in the present serum composition induces blood coagulation was studied. In the same manner as in Examples 6 and 7, mesenchymal stem cells derived from human amnion membrane and cultured in aMEM medium added with the present serum composition by 10% of the medium were adjusted with saline to $1 \times 10^5$ cells/ml. As the control, the same cells cultured in aMEM medium added with fetal bovine serum by 10% of the medium were used. To these cell suspensions (160 μL) was added human plasma (40 μL), and the mixture was incubated at 37° C. for 5 min. Thereto was added 20 μM CaCl$_2$ (100 μL) and the coagulation time was measured by a blood coagulation automatic measuring apparatus (KCl Delta, manufactured by Tcoag). The results are shown in Table 32.

TABLE 32

| | coagulation time (sec) |
|---|---|
| fetal bovine serum | 24.5 |
| present serum composition | 44.7 ± 0.5 |

The mesenchymal stem cells derived from human amnion membrane and cultured in the present serum composition prolonged the coagulation time as compared to fetal bovine serum. They were found to not induce blood coagulation with ease.

Example 9

Thus, studies were conducted to search for the reason that the cell cultured in the present serum composition does not induce blood coagulation easily. The concentration of a tissue factor pathway inhibitor (TFPI), which is a strong anticoagulate factor secreted by cells and bound to the plasma membrane, in the culture supernatant of mesenchymal stem cells derived from human amnion membrane (passage number 4) and cultured in aMEM medium added with the present serum composition by 10% of the medium was measured using an ELISA kit (Human TFPI Quantikine ELISA Kit) (DTFP10, R&D systems). As the control, the culture supernatant of the same cells cultured in aMEM medium added with fetal bovine serum by 10% of the medium and these media before cell culture. The results are shown in Table 33.

TABLE 33

| | TFPI concentration (pg/ml) | |
|---|---|---|
| culture of mesenchymal stem cells derived from human amnion membrane | none | yes |
| fetal bovine serum | below detection sensitivity | 45.1 |
| present serum composition | below detection sensitivity | 63.1 |

The mesenchymal stem cells derived from human amnion membrane cultured in the present serum composition secreted more TFPI as compared to fetal bovine serum. Thus, it was found that they do not easily induce blood coagulation.

INDUSTRIAL APPLICABILITY

They can be utilized for the production of a serum composition.

The invention claimed is:
1. A method for producing a bovine serum composition, comprising
    (1) a step of obtaining a buffy coat and a fraction containing leukocytes, platelets, and erythrocytes and having a heavier specific gravity than that of the buffy coat by continuous centrifugation from bovine whole blood anticoagulated with an anticoagulant, and
    (2) a step of promoting an interaction between leukocytes and platelets in the fraction obtained in the step (1) and activating same by incubating the fraction at a given temperature for not less than a given time to cause secretion or release of a humoral factor from the leukocytes and/or platelets, and performing a recoagulation treatment of blood components including the humoral factor with a re-coagulating agent,
    wherein the fraction with a heavier specific gravity than that of the buffy coat is a fraction having a higher leukocyte concentration than that of the buffy coat.
2. The production method according to claim 1, wherein the fraction with a heavier specific gravity than that of the buffy coat is a fraction with a specific gravity of 1.071-1.084.

3. The production method according to claim 2, wherein the given temperature is ambient temperature to 40° C. and the time is not less than 5 min.

4. The production method according to claim 3, wherein the leukocytes and platelets are further activated by adding a glass material.

5. The production method according to claim 4, wherein the anticoagulant is sodium citrate or citric acid.

6. The production method according to claim 5, wherein the re-coagulating agent is a calcium chloride solution.

7. The production method according to claim 6, wherein the humoral factor is one or more factors selected from the group consisting of TGF-beta1, Basic FGF, Eotaxin, G-CSF, IFN-gamma, IL-10, IL-12(p70), IL-13, IL-1RA, IL-1b, IL-4, IL-5, IL-6, IL-8, IL-9, IP-10, MCP-1, PDGF-BB, and TNF-alpha.

8. The production method according to claim 1, wherein the given temperature is ambient temperature to 40° C. and the time is not less than 5 min.

9. The production method according to claim 1, wherein the leukocytes and platelets are further activated by adding a glass material.

10. The production method according to claim 1, wherein the anticoagulant is sodium citrate or citric acid.

11. The production method according to claim 1, wherein the re-coagulating agent is a calcium chloride solution.

12. The production method according to claim 1, wherein the humoral factor is one or more factors selected from the group consisting of TGF-beta1, Basic FGF, Eotaxin, G-CSF, IFN-gamma, IL-10, IL-12(p70), IL-13, IL-1RA, IL-1b, IL-4, IL-5, IL-6, IL-8, IL-9, IP-10, MCP-1, PDGF-BB, and TNF-alpha.

13. A method for culturing a human mesenchymal stem cell or human mesenchymal cell, comprising culturing the cell in the presence of the bovine serum composition made by the production method of claim 1.

14. The method according to claim 13, wherein the cell does not induce blood coagulation as compared to culturing in the presence of fetal bovine serum.

* * * * *